US010278393B2

(12) United States Patent
Bobbert

(10) Patent No.: US 10,278,393 B2
(45) Date of Patent: May 7, 2019

(54) METHOD FOR DISINFECTING A SURFACE, AND COMPOSITION SUITABLE FOR USE THEREIN

(71) Applicant: HYGIENIX BV, Hilversum (NL)

(72) Inventor: Ilja Bobbert, Hilversum (NL)

(73) Assignee: HYGIENIX BV, Hilversum (NL)

( * ) Notice: Subject to any disclaimer, the term of this patent is extended or adjusted under 35 U.S.C. 154(b) by 0 days.

(21) Appl. No.: 15/548,383

(22) PCT Filed: Feb. 5, 2016

(86) PCT No.: PCT/EP2016/052551
§ 371 (c)(1),
(2) Date: Aug. 2, 2017

(87) PCT Pub. No.: WO2016/124764
PCT Pub. Date: Aug. 11, 2016

(65) Prior Publication Data
US 2018/0027812 A1  Feb. 1, 2018

(30) Foreign Application Priority Data
Feb. 5, 2015  (EP) .................................... 15154007

(51) Int. Cl.
A01N 25/30 (2006.01)
A01N 31/02 (2006.01)
A01N 33/08 (2006.01)
A01N 37/10 (2006.01)
A01N 37/36 (2006.01)
A01N 37/40 (2006.01)
A01N 37/46 (2006.01)
A01N 41/02 (2006.01)
A01N 47/34 (2006.01)
A01N 47/36 (2006.01)
A01N 59/00 (2006.01)
A01N 59/26 (2006.01)
A01N 65/42 (2009.01)
A01N 65/44 (2009.01)

(52) U.S. Cl.
CPC ............. A01N 37/46 (2013.01); A01N 31/02 (2013.01); A01N 33/08 (2013.01); A01N 37/10 (2013.01); A01N 37/36 (2013.01); A01N 37/40 (2013.01); A01N 41/02 (2013.01); A01N 47/34 (2013.01); A01N 47/36 (2013.01); A01N 59/00 (2013.01); A01N 59/26 (2013.01); A01N 65/42 (2013.01); A01N 65/44 (2013.01)

(58) Field of Classification Search
CPC ........ A01N 37/36; A01N 59/00; A01N 25/30; A01N 37/46; A01N 31/02; A01N 33/08; A01N 37/10; A01N 37/40; A01N 41/02
See application file for complete search history.

(56) References Cited

U.S. PATENT DOCUMENTS

| | | | | | |
|---|---|---|---|---|---|
| 4,749,515 A | * | 6/1988 | Miyamoto | ............. | A61K 8/466 510/126 |
| 2010/0197553 A1 | * | 8/2010 | Barnabas | ............... | C11D 1/662 510/236 |
| 2016/0317424 A1 | * | 11/2016 | Kadir | .................... | A61Q 5/006 |

FOREIGN PATENT DOCUMENTS

| | | | |
|---|---|---|---|
| DE | 198 38 034 A1 | 2/2000 | |
| EP | 0 256 656 A1 | 2/1988 | |
| EP | 1 074 247 A2 | 2/2001 | |
| EP | 1 221 313 A2 | 7/2002 | |
| EP | 1 266 571 A1 | 12/2002 | |
| FR | 2956813 A1 * | 9/2011 | ............... A61K 8/33 |
| WO | 03/039496 A1 | 5/2003 | |
| WO | 2008/071746 A1 | 6/2008 | |

OTHER PUBLICATIONS

FR-2956813-A1, Espacenet English translation, downloaded Feb. 2019 (Year: 2019).*
Anon, "The Use of N-Acyl Sarcosinate Surfactants in Personal Care Products," May 1, 2000, [http://www.dewolfchem.com/pdf/Chattem_Personal_Care_Brochure.pdf].
Mar. 18, 2016 International Search Report issued in International Patent Application No. PCT/EP2016/052551.
Mar. 18, 2016 Written Opinion of the International Searching Authority issued in International Patent Application No. PCT/EP2016/052551.
Aug. 8, 2018 Office Action issued in European Patent Application No. 16 703 306.7.

(Continued)

Primary Examiner — Mark V Stevens
(74) Attorney, Agent, or Firm — Oliff PLC

(57) ABSTRACT

A method for disinfecting a surface contaminated with microorganisms or suspected of being contaminated with microorganisms, the microorganism being one or more of *Escherichia coli, Staphylococcus aureus, Pseudomonas aeruginosa*, and *Enterococcus hirae*, including the step of contacting the surface with a disinfecting composition including: 0.1-10 wt. % of one or more N-acylated amino acids or N-acylated peptides, or a salt thereof, less than 0.1 wt. % of hydrogen peroxide, 0.1-20 wt. % of one or more non-ethoxylated anionic surfactants, 0.05-5 wt. % of a carboxylic acid, wherein the disinfecting composition has a pH in the range of 1-4.5 wherein the composition includes less than 5 wt. % of ethoxylated anionic surfactant. The invention also pertains to a composition suitable for use in the method according to the invention. The method and composition provide excellent biocidal activity over a broad range of organisms using low concentrations of organic acids.

18 Claims, No Drawings

(56) References Cited

OTHER PUBLICATIONS

Xia et al., "Structure-Function Relationship of Acyl Amino Acid Surfactants: Surface Activity and Antimicrobial Properties," Journal of Agricultural and Food Chemistry, vol. 43, 1995, pp. 867-871.
Baba et al., "Antibacterial Screening of Some Synthesized Palmitoyl Amino Acids and Their Aromatic Analogues," British Journal of Pharmaceutical Research, vol. 4, No. 4, 2014, pp. 513-519.

* cited by examiner

METHOD FOR DISINFECTING A SURFACE, AND COMPOSITION SUITABLE FOR USE THEREIN

The present invention pertains to a method for disinfecting a surface which is contaminated with microorganisms or which is suspected of being contaminated with microorganisms, the microorganism being one or more of *Escherichia coli, Staphylococcus aureus, Pseudomonas aeruginosa*, and *Enterococcus hirae*. The invention also pertains to a composition suitable for use therein.

The microorganisms *Escherichia coli, Staphylococcus aureus, Pseudomonas aeruginosa*, and *Enterococcus hirae* together form the standard set of organisms against which a disinfecting composition is to be effective. For example, *Pseudomonas aeruginosa* is often seen as an important organism to kill when providing "hospital-grade" disinfectants for use in healthcare settings. For example the United States Environmental Protection Agency (EPA) requires proven efficacy against *Pseudomonas aeruginosa* to make hospital disinfection claims. *Escherichia coli* is important to address in view of its wide-spread existence, in combination with its infection properties, and for some antibiotic resistant strains the difficulties of treating infections with this organism. *Staphylococcus aureus* is of particular concern in hospital situations, especially where it is present as Methicillin Resistant *Staphylococcus aureus* (MRSA). *Enterococcus hirae* is also of particular concern in hospital situations. It is a representative organism in tests for the pathogenic and antibiotics resistant Vancomycin Resistant Enterococci (VRE).

The four cited organisms are each very different in their response to disinfectants and antimicrobials, and it is well known in the art that compositions which are active against one of these organisms are not necessarily effective against the other organisms. It is important that disinfecting or antimicrobial products have broad spectrum efficacy as it is most of time unknown what pathogens are present on surfaces or skin. There is a clear need in the art for disinfecting compositions which show activity against all four of these organisms.

The issue becomes more complicated by the other considerations which a disinfecting composition should meet. Well known and broad spectrum biocidal active ingredients are alcohols, chlorine, peracetic acid, quaternary ammonium compounds, biguanides and triclosan. All of these ingredients have severe drawbacks either in material compatibility (peracetic acid, chlorine, alcohols), flammability (alcohols), metal corrosion (peracetic acid, chlorine), skin irritation (quaternary ammonium compounds, peracetic acid, chlorine, biguanides), respiratory tract irritation (alcohols, peracetic acid, chlorine), causing microbial resistance (quaternary ammonium compounds, biguanides, Triclosan), are suspect carcinogenic to humans and/or animals (Triclosan) or are environmentally burdening (Chlorine, Peracetic acid) or even persistent in the environment (Triclosan, quaternary ammonium compounds) It is therefore clear that these traditional biocidal active compounds are not sustainable in the long term and that there is a need for safer, more sustainable and more gentle solutions to eradicate pathogens, which should, however, be combined with a broad spectrum activity against the key group of *Escherichia coli, Staphylococcus aureus, Pseudomonas aeruginosa*, and *Enterococcus hirae*.

It has been found that this problem is solved by the present invention.

The present invention pertains to a method for disinfecting a surface which is contaminated with microorganisms or which is suspected of being contaminated with microorganisms, the microorganism being one or more of *Escherichia coli, Staphylococcus aureus, Pseudomonas aeruginosa*, and *Enterococcus hirae*, comprising the step of contacting the surface with a disinfecting composition comprising:
    0.1-10 wt. % of one or more N-acylated amino acids or N-acylated peptides, or a salt thereof,
    less than 0.1 wt. % of hydrogen peroxide,
    0.1-20 wt. % of one or more non-ethoxylated anionic surfactants,
    0.05-5 wt. % of a carboxylic acid,
wherein the disinfecting composition has a pH in the range of 1-4.5, wherein the composition comprises less than 5 wt. % of ethoxylated anionic surfactant.

The present invention also pertains to a disinfecting composition suitable for disinfecting a surface which is contaminated with microorganisms or which is suspected of being contaminated with microorganisms, the microorganism being one or more of *Escherichia coli, Staphylococcus aureus, Pseudomonas aeruginosa*, and *Enterococcus hirae*, the composition comprising
    0.1-10 wt. % of one or more N-acylated amino acids or N-acylated peptides, or a salt thereof,
    less than 0.1 wt. % of hydrogen peroxide,
    0.1-20 wt. % of one or more non-ethoxylated anionic surfactants,
    0.05-5 wt. % of carboxylic acid,
wherein the disinfecting composition has a pH in the range of 1-4.5, wherein the composition comprises less than 5 wt. % of ethoxylated anionic surfactant.

It has been found that it is the specific combination of N-acylated amino acids or N-acylated peptides with non-ethoxylated anionic surfactants, the presence of a carboxylic acid, and the specified pH which makes a composition active against the combined set of microorganisms.

It has further been found that the presence of an ethoxylated anionic surfactant is to be limited or, as will be discussed further below, to be prevented. It has been found that, contrary to earlier expectations, these compounds do not contribute to achieving a biocidal effect. Reference is made to Example 3 of the present application, where it is shown that a composition comprising triethanolamine lauryl sulphate shows biocidal activity against *E. coli, S. aureus*, and *E. hirae*, while otherwise comparable compositions which contain sodium laureth sulphate or zinc laureth sulphate show no such activity. This is particularly surprising for zinc laureth sulphate, as the presence of zinc is often related to biocidal activity.

If one of these requirements is not met, an active composition is not obtained. It is interesting to note that the specific combination of these components makes it possible to have an effective composition without the presence of hydrogen peroxide. While H2O2 is often an attractive biocidal compound, it is unstable and difficult to store for longer periods at ambient temperatures, and it may be associated with corrosive or irritating activity on some surfaces, eyes and skin. Therefore, a disinfecting composition which contains only a limited amount of H2O2 is a desirable feature.

An advantage of the composition of the invention is that it provides excellent biocidal activity over a broad range of organisms using low concentrations of organic acids. Further, the composition can be applied without handling or usage precautions and safety measures, and does not require rinsing or only scarce rinsing after application. it is a further advantage of the composition according to the invention that it provides a synergistic broad spectrum biocidal solution without the use of peracetic acid, which causes an undesirable pungent odor and is very irritating to eyes, skin and respiratory tract.

To build effective cleaning liquids or soaps, surfactants are required to enhance wetting and cleaning ability, as well as to regulate foaming behavior. In order for the biocidal product to be safe and non-hazard classified, the specific organic acids should be combined with the acylated amino acids or acylated peptides and the non-ethoxylated surfactants to create strong synergies. Optimally, all of the ingredients need to be present at low concentrations.

These low concentrations are critical because of the desired safety profile of the product. A hazard classification prescribing to wear one or more of protective gloves, protective clothing, eye protection, or face protection while using the product is in reality impossible or at least highly unpractical for users. Washing hands with a product that requires the user to wear gloves because of a hazard qualification while handling and using the product is highly unrealistic. However, the low concentrations required to avoid such hazard classification create substantial challenges. The lower the concentration of active ingredients and surfactants, the less efficacious the product becomes. Also its cleaning ability and foaming behavior will substantially deteriorate. In order to boost efficacy and foaming behavior, a person skilled in the art would be tempted to increase the levels of both active ingredients and surfactants, thereby compromising the safety profile of the product and causing the product to be classified as a hazardous substance with use precautions under CLP or GHS.

Surprisingly, it has now been found that combinations of acylated amino-acids or acylated peptides with non-ethoxylated surfactants at a specific pH, all at relatively low concentrations results in high antimicrobial activity, good foaming and cleaning ability of the compositions, but at the same time no hazard classification. These products are safe to use on multiple surfaces and on the human body. The skin irritation potential is very low, while the cleaning and foaming behavior is acceptable to very good.

A further advantage of the present invention is that the composition can be so mild that it can be used frequently throughout the day, to allow people to disinfect, e.g., their hands frequently without dryness or redness of the skin occurring to an unacceptable extent. A further advantage of the composition according to the invention is that it combines broad spectrum activity with being gentle to skin and surfaces and environmentally sustainable.

In one embodiment, the surface to be treated with the method according to the invention is contaminated or suspected to be contaminated with *Escherichia coli, Staphylococcus aureus, Pseudomonas aeruginosa*, and *Enterococcus hirae*.

The method and composition according to the invention will be discussed in more detail below.

The composition comprises 0.1-10 wt. % of one or more N-acylated amino acids or N-acylated peptides, or a salt thereof. It may be preferred for the composition to comprise 0.2-8 wt. % of this compound, in some embodiments 0.2-5 wt. %. If the amount of N-acylated amino acid or N-acylated peptide is too low, the effect of the present invention will not be obtained. On the other hand, if the amount is too high, no additional effect will be obtained.

The term "N-acylated amino acid and/or peptide" according to the invention refers to peptides and/or free amino acids, or salts thereof, wherein at least 50% of the amino groups of the free amino acids and/or of the peptides, is acylated. Preferably, all the amino groups are acylated. The amino acid may be a single amino acid or may be a mixture of amino acids obtainable by hydrolysis of a suitable protein substrate. In the latter case, short peptides may be present, typically comprising peptides with an average molecular weight lower than about 4000 Dalton, preferably lower than about 2000 Dalton.

The N-acylated peptide and/or N-acylated amino acid to be used according to the invention preferably has a structure according to Formula I as follows:

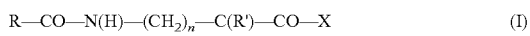
$$R\text{—}CO\text{—}N(H)\text{—}(CH_2)_n\text{—}C(R')\text{—}CO\text{—}X \quad (I)$$

or a salt thereof, wherein R—CO— represents an acyl group wherein R is a saturated or unsaturated, straight of branched C5 to C21 radical, n is 0, 1 or 2, R' represents an amino acid side chain, and X is OH or a group according to Formula II:

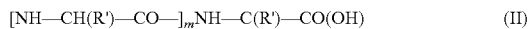
$$[NH\text{—}CH(R')\text{—}CO\text{—}]_m NH\text{—}C(R')\text{—}CO(OH) \quad (II)$$

wherein m ranges from 0 to such a value that the compound of Formula II specifies a peptide having an average molecular weight of about 100 to about 3900 Dalton, preferably of about 100 to about 1900 Dalton, more preferably about 100 to about 1300, most preferably about 100 to about 700 Dalton.

Suitable salts are those wherein the dissociated carboxylic groups are neutralised with cations belonging to the group of alkaline metals and alkaline earth metals, ammonia, other metals such as lead, iron, aluminum, manganese, copper, zinc, or by organic bases such as arginine, lysine, mono-, di-, or tri-ethanolamine, ornithine, histidine, morpholine, or choline. Such neutralising cations can be utilised also in combinations with one another.

Preferably, the R moiety of the acyl group is a C6 to C20 radical. More preferred are the straight chain variants thereof (saturated as well as unsaturated). Especially preferred acyl groups are octanoyl (capryloyl), nonanoyl, decanoyl, undecanoyl, undecylenoyl, dodecanoyl (lauroyl), tridecanoyl, tetradecanoyl (myristyl), hexadecanoyl (palmitoyl), octadecanoyl (stearoyl), oleoyl, and mixtures thereof.

When X is OH, the compound of Formula I represents an amino acid. According to the invention, the term "amino acid" may refer to an alpha-, beta- or gamma-amino acid, i.e. n is 0, 1 or 2, but preferably is an alpha-amino acid (n is 0).

R' represents an amino acid side chain occurring in natural proteogenic amino acids, or a side chain that is modified as compared to those occurring in natural proteogenic amino acids by substitution of a hydrogen atom in the side chain for a hydroxyl, methyl, ethyl or other suitable group.

A proteogenic amino acid is an amino acid that is encoded by DNA. An example of a modified amino acid is hydroxyproline, occurring for instance in collagen.

Preferred amino acid precursors for the N-acylated compounds of Formula I wherein X is OH are chosen from the group of polar amino acids, such as glutamic acid, glutamate, aspartic acid, glutamine, glycine, asparagine, taurine, lysine, arginine, histidine, proline, sarcosine, threonine, serine.

Especially preferred amino acids are glutamic acid, glutamate, sarcosine, glycine, aspartic acid, lysine.

When X is a compound of Formula II, X represents an amino acid unit when m is 0 or a peptide when m is ≥1. The value of m may typically range from 1 to 18 for X to specify a peptide with a molecular weight from about 200 to about 1900 Dalton.

Preferred peptide and/or amino acid precursors for the N-acylated compounds of Formula I are protein hydrolysates. Protein hydrolysates are degradation products of protein substrates, and typically are obtained by acidic, alkaline and/or enzymatic hydrolysis of a protein substrate, thereafter having an average molecular weight of 100 to 2000, preferably 100 to 1400 and more particularly 100 to 800. Most preferably, the protein substrate is predominantly hydrolysed to the individual constituting amino acids, preferably wherein the individual amino acids constitute at least 50% (w/w) of the protein hydrolysate.

Suitable protein substrates for example are vegetable proteins, like wheat, rice, soya, sunflower, maize, pea, almond and potato protein; animal proteins, like milk, gelatin, collagen, keratin protein; microbial proteins, like algal, yeast of fungal protein.

Protein substrates may be chosen based on their amino acid composition. Preferably, the protein substrate has a high level of glutamic acid/glutamine residues, leading to a protein hydrolysate with a high glutamic acid content. An example of such a preferred protein substrate is wheat protein.

The compounds according to Formula I are conveniently obtained by N-acylation of the amino acid and/or peptide precursors as described above, using carboxylic activated derivatives of the fatty acid of formula RCOOH, R being defined as above, by standard methods known in the art. Such derivatives are for example the symmetric anhydrides of these acids or acid halides.

N-acylated amino acids and their salts that may be mentioned, for example, are those of N-acylglutamate, such as monosodium cocoylglutamate, monosodium lauroylglutamate, disodium C14-C20 alkylglutamate, the C14-C20 alkyl radical being derived from hydrogenated tallow, sold respectively under the names "Acylglutamate CS-11", "Acylglutamate LS-11" and "Acylglutamate HS-21" by Ajinomoto. Examples of acylglutamates also include sodium cocoylglutamate and sodium laurylglutamate sold by Clariant under the Hostapon CCG/CLG/KCG trade names and Protelan AG 8 (capryloylglutamate) and Protelan AGL 95 (sodium lauroylglutamate) and Protelan AGL 5/C (sodium cocoylglutamate) of Zschimmer & Schwarz.

Mention may also be made of N-acyl sarcosinates, such as lauryl sarcosinate, commercially available under the tradename Protelan LS9011 from Zschimmer & Schwarz and Crodasinic LS30 and Crodasinic LS95 from Croda. Mention may also be made of N-acyl lysines such as lauroyllysine sold under the name "Amihope LL" by Ajinomoto.

Among the N-acylated hydrolysed proteins that may be mentioned are those derived from all or part of collagen or keratin, such as sodium lauroyl collagen and palmitoyl keratin sold under the names "Proteol B 30" and "Lipacide PK" by the company SEPPIC, or from wheat, such as potassium undecylenoyl hydrolysed wheat protein sold as "Protelan AG 11" by Zschimmer & Schwarz.

The compositions as described herein may contain mixtures of two or more of the N-acylated products mentioned above.

The composition of the invention comprises 0.1-20 wt. % of one or more non-ethoxylated anionic surfactants. It may be preferred for the amount of non-ethoxylated anionic surfactant to be in the range of 0.2-15 wt. %, in particular in the range of 0.5-10 wt. %, more in particular 0.5-8 wt. %. If the amount of non-ethoxylated anionic surfactant is too low, the effect of the present invention will not be obtained. On the other hand, if the amount is too high, the composition may become corrosive to skin or surfaces, which is an undesired effect of a biocidal product.

The term "non-ethoxylated anionic surfactant" according to the invention refers to anionic surfactants that do not contain one or more ethoxy-groups. Anionic surfactants carry an anionic charge, or have anionic character in an acidic environment. Examples of these non-ethoxylated anionic surfactants, are the following surfactant types, whereby this list is in no way exhaustive and is meant purely for illustrative purposes: salts of alkyl sulphates or phosphates, alkyl sulphates or phosphates with amine counterions, such as triethanolamine and mono isopropanolamine, for example triethanolamine lauryl sulfate and monoisopropanolamine lauryl sulphate; salts of alkyl carboxylates, such as Sodium Lauryl Glucose Carboxylate and Sodium Lauryl Glycol Carboxylate; salts of alkyl lactylates, such as Sodium Lauroyl Lactylate; salts of alkyl sulfoacetate, such as Sodium Lauryl Sulfoacetate; salts of alkylsulfosuccinate, such as Sodium Lauryl Sulfosuccinate; salts of sulfolaurate, such as Sodium Methyl 2-Sulfolaurate and Disodium 2-Sulfolaurate; anionic alkylpolyglucosides, such as Disodium Cocopolyglucose Citrate, Disodium Cocopolyglucose Sulfosuccinate, Sodium Co-copolyglucose Tartrate; salts of alkyl taurate, such as Sodium Lauryl Taurate and Sodium Cocoyl Taurate; salts of alkyl isethionate, such as Sodium Lauroyl Isethionate and Sodium Co-coyl Isethionate, etc.

The use of alkyl sulphates as anionic surfactant may be preferred. In one embodiment of the present invention the non-ethoxylated anionic surfactant comprises an alkyl sulphate salt, wherein the alkyl chain comprises 4-22 carbon atoms, in particular 8-18 carbon atoms, more in particular 10-18 carbon atoms. In one embodiment, the alkyl group is a lauryl group (C12, lauryl sulphate), cocoyl group (a mixture of C10-C18 alkyl groups derived based on the composition of coconut oil), or myrystyl group (C14, myristyl sulphate). The counterion of the salt is preferably selected from sodium, potassium, ammonium, calcium, magnesium, zinc, and organic amine groups, such as mono-, di-, or tri-alkylamines, where the amine group has 1-4 carbon atoms. Preferably, in the instance that the salt is an amine salt, the alkyl sulphate salt is a monoisopropanolamine salt, a triethanolamine salt, a sodium salt, or an ammonium salt.

The presence of a non-ethoxylated anionic surfactant is a particular feature of the present invention. It has been found that if a non-ethoxylated anionic surfactant is used in a composition instead of an ethoxylated anionic surfactant, a better broad-spectrum biocidal activity is obtained.

As indicated above, the composition according to the invention comprises less than 5 wt. % of ethoxylated anionic surfactant. The presence of a limited amount of this compound may be acceptable as it may have an effect of reducing skin irritancy, cleaning or foaming performance. However, as it does not contribute to biocidal performance, it may be preferred to limit the amount, e.g., to less than 3 wt. %, in particular less than 2 wt. % of ethoxylated anionic surfactant. In some embodiments, the composition comprises less than 1 wt. % of ethoxylated anionic surfactant. It may also be that the composition is substantially free of ethoxylated anionic surfactant, with the wording "substantially free" meaning that no ethoxylated anionic surfactant is added on purpose. Contaminant amounts of non-ethoxylated anionic surfactant may be present in as far they cannot be prevented.

The composition of the present invention comprises 0.05-5 wt. % of one or more carboxylic acids, preferably 0.1% to 5 wt. %, more preferably 0.2-5 wt. %, and most preferably 0.2%-3 wt. %. The carboxylic acid is present on the one hand to bring the composition to the desired pH. On the other hand, it also contributes to the broad-spectrum biocidal effect of the composition according to the invention. If the amount of carboxylic acid is too low, the effect of the present invention will not be obtained. On the other hand, if the amount is too high, an increase of biocidal effect may not be obtained, whereby the mildness of the composition may also be detrimentally affected.

In one embodiment, one or more carboxylic acids are used having 2 to 10, in particular 3 to 6 carbon atoms. In one embodiment, the carboxylic acid is a mono-, di-, or tricarboxylic acid. It may be preferred for the carboxylic acid to be a hydroxy-carboxylic acid, in particular an alpha- or beta-hydroxycarboxylic acid. Examples of suitable carboxylic acids include citric acid, lactic acid, glycolic acid, tartaric acid, malic acid, maleic acid, fumaric acid, adipic acid, and succinic acid. Citric acid, lactic acid, tartaric acid, and malic acid may be preferred. Combinations of acids may also be used.

In one embodiment, one or more of the carboxylic acids is a cyclic carbocxylic acid, e.g., selected from the group of 2-furan-dicarboxylic acid, (iso)phtalic acid, furoic acid, salicylic acid and/or benzoic acid. It may be preferred for the cyclic carboxylic acid to be salicylic acid or benzoic acid. Combinations of acids may also be used.

It has been found that particularly attractive results can be obtained when the composition comprises at least one of the following carboxylic acids: lactic acid, glycolic acid, benzoic acid, and tartaric acid. It may be preferred for these acids to provide at least 50 wt. % of the total carboxylic acid present in the system, in particular at least 70 wt. %, in some embodiments at least 90%.

The composition of the present invention has a pH in the range of 1-5. If the pH of the composition is too high, the broad spectrum biocidal activity of the present invention will not be obtained. If the pH is too low, the composition may detrimentally affect skin and surfaces. It is preferred for the pH to be in the range of 2-4.5.

The term "surface" in the present specification comprises any animate or inanimate, hard or soft surface.

Where the surface to be disinfected with the composition of the invention is a surface of an animal or human body, e.g., skin, hair, or mucous membranes, it is preferred for the pH of the disinfecting composition to be in the range of 3-4.5, in particular 3-4. It has been found that a pH in this ranges provides an optimum balance between a broad spectrum disinfecting activity on the one hand, while preventing irritation of the surface.

Where the surface is an inanimate surface, for example hard or soft inanimate surfaces such as tabletops, walls, floors, equipment, instruments, curtains, bed linen, clothing, etc., it may be preferred for the disinfecting composition to have a pH in the range of 1-4, in particular 2-4.

The compositions as described herein may further comprise one or more further surfactants, such as an amphoteric, cationic and/or non-ionic surfactants.

Suitable amphoteric surfactants include amphoteric alkyl polyglucosides, alkyl betaines, alkyl amidopropyl betaines, alkyl amidopropyl betaine amides, alkyl sulfobetaines, amine oxides, amphocarboxyacetates, amphocarboxydiacetates, amphocarboxypropionates, amphocarboxydipropionates, and/or derivates thereof.

It may be preferred for the total amount of amphoteric surfactant to be at most 10 wt. %, in particular at most 8 wt. %, more in particular at most 4 wt. %. If present, the amount of amphoteric surfactant generally is at least 0.2 wt. %, in particular at least 0.5 wt. %.

Suitable cationic surfactants include skin conditioning cationic polymers, preferably from the polyquarternium-type surfactants, such as comprising MethacrylAmidoPropyl Trimethyl Ammonium Chloride, DiAllyl DiMethyl Ammonium Chloride or MethAcryloyloxyethyl Trimethyl Ammonium MethylSulfate groups.

It may be preferred for the total amount of cationic surfactant in the composition of the present invention to be at most 3 wt. %, in particular at most 2 wt. %, more in particular at most 1 wt. %. If used, the total amount of cationic surfactant is, e.g., at least 0.05 wt. %, in particular at least 0.1 wt. %.

Suitable non-ionic surfactants include amides, ethoxylated and non-ethoxylated fatty amines, ethoxylated nonylphenols, APGs (alkylpolyglucosides), AEGs (alkylethoxyglucosides), esters/ethers of fatty acids with glycerol and/or ethoxylated and non-ethoxylated sugars, ethoxylated/propoxylated and non-ethoxylated/propoxylated esters, ethoxylated/propoxylated and non-ethoxylated/propoxylated fatty alcohols.

It may be preferred for the total amount of non-ionic surfactant in the composition of the present invention to be at most 3 wt. %, in particular at most 2 wt. %, more in particular at most 1 wt. %. If used, the total amount of no-ionic surfactant is, e.g., at least 0.1 wt. %, in particular at least 0.3 wt. %.

The compositions as described herein further may contain the usual ingredients for compositions for use on the skin. For instance, the composition may include skin conditioners, skin emollients, refatting agents, stabilizers, pearlizing agents, thickening agents, preservatives, coloring agents or dyes and perfumes.

Skin emollients and refatting agents may for example include glycerol, betaine, panthenol, glycerides, polyglycerol, aloe vera, vitamin E, sorbitol, allantoin, cationics, polymers, castor oil, lanolin and its derivatives and cetyl alcohol. The composition may be thickened via the methods known to the man skilled in the art, for example by addition of Sodium Chloride or a combination of Sodium Chloride and specific types of surfactants (such as Sodium Lauryl Ether Sulfate or Betaines), or by addition of (hydroxy) cellulose based or (cross-) polymer based thickening agents. Preferably, the composition is thickened by the use of (hydroxy)cellulose based or polymer based thickening agents, such as Klucel types (Hercules Chemicals), Natrosol types (Hercules Chemicals), Carbopol types (Noveon), or Oxetal VD 92 of Zschimmer & Schwarz. Via these methods, and adjustment of pH range, a whole range of viscosity levels may be achieved.

The composition of the present invention may be preserved by the use of preservatives, for example parabens, benzyl alcohol, phenoxyethanol, cationics, sorbic acid, methylisothiazolinone, caprylyl glycol, benzoic acid, potassium benzoate, salicylic acid, potassium salicylate, etc. The composition of the present invention may also comprise a sequestering agent, such as a cation sequestering agent chosen from ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), and salts thereof, acetanilide, trisodium ethylenediamine disuccinate, tetrasodium iminodisuccinate, phosphonic acid derivatives having 1 to 5 phosphonic acid groups, for instance a Dequest phosphonate (Solutia), 1-hydroxyethylidene-1,1-diphosphonic acid (HEDP), amino tri(methylene phosphonic acid), diethylenetriamine-penta(methylene phosphonic acid), 2-hydroxy ethylimino bis(methylene phosphonic acid), and ethylene diamine tetra(methylene phosphonic acid).

The compositions as described herein may be in the form of an aqueous solution or an emulsion, such as a lotion, a foam, a liquid soap, a spray, a gel, a cream, and the like, or in the form of an impregnated wipe.

In one embodiment, the composition is an aqueous solution, which can have a varying degree of viscosity.

In a preferred embodiment, the composition is applied as a foam or a gel in order to increase contact time and avoid spilling or dripping of the required dose off the surface or off the skin, as may be the case when using a spray formulation. For example in the case of applying the composition on hands or skin without additional water being added (hand sanitizer) or as a teat dip to disinfect cow teats. The use of the non-ethoxylated anionic surfactants and N-acylated amino acids in the compositions as described herein already provides foaming capacity to the composition.

Advantageously, the compositions as described herein have a favourable environmental profile. Also advantageously, the compositions as described herein are able to provide adequate levels of disinfection while not being corrosive to surfaces, or irritating to the skin or mucous membranes. The compositions are non-irritating to skin due to the inclusion of highly skin compatible N-acylated amino acids/protein hydrolysates, mild surfactant package and low concentrations of other mild additives, which may be employed as described above. The composition has broad-spectrum activity, the degree of which is unexpected given the only low to mediocre germicidal activity of the individual ingredients. In particular, the composition has bactericidal, yeasticidal and enveloped virucidal activity. A synergy exists amongst the ingredients of the present compositions such that an effective disinfectant is provided that is highly suitable for use on surfaces, mucous membranes and skin.

The composition according to the invention is particularly attractive for cleaning surfaces in a healthcare environment, where its broad spectrum activity against all of *Escherichia coli, Staphylococcus aureus, Pseudomonas aeruginosa*, and *Enterococcus hirae* is of particular benefit. It can, however, also be used in situations where but one, two, or three of the organisms are an issue.

It can, e.g., be used as disinfectant for skin or mucous membranes in healthcare environments, such as cleaner disinfectant spray, cleaner disinfectant wipe, disinfectant gel, hand soap, an antimicrobial shower gel, an impregnated wipe, or for intimate hygiene solutions.

The composition according to the invention can also be used for cleaning inanimate surfaces, such as surfaces in healthcare environments, including floors, walls, instruments, equipment, doors, work surfaces such as table tops and furniture, and also textile materials like carpets, curtains, and laundry, e.g., as laundry cleaner, laundry disinfectant or laundry deodorizer.

If so desired, the composition can be removed from the surface after use, e.g., by wiping or rinsing the surface. It is also possible to leave the surface to airdry without removing the composition therefrom by wiping or rinsing.

It has been found that the present invention finds particular use in cleaners for inanimate hard surfaces, in one embodiment, the invention pertains to a method for disinfecting an inanimate hard surface which is contaminated with microorganisms or which is suspected of being contaminated with microorganisms, the microorganism being one or more of *Escherichia coli, Staphylococcus aureus, Pseudomonas aeruginosa*, and *Enterococcus hirae*, comprising the step of contacting the surface with a disinfecting composition comprising:
- 0.1-3 wt. %, in particular 0.1-2 wt. %, of one or more N-acylated amino acids or N-acylated peptides, or a salt thereof,
- less than 0.1 wt. % of hydrogen peroxide,
- 0.1-3 wt. %, in particular 0.1-2 wt. %, of one or more non-ethoxylated anionic surfactants,
- 0.05-2 wt. %, in particular 0.05-1 wt. %, of a carboxylic acid, wherein the disinfecting composition has a pH in the range of 1-3.5, in particular 1-3, wherein the composition comprises less than 2 wt. % of ethoxylated anionic surfactant, in particular less than 1 wt. %, more in particular less than 0.5 wt. %. For preferences as regards the nature of the various components, reference is made to what is stated above.

It has been found that this composition combines a high biocidal efficacy with low streaking, which is of particular importance on hard surfaces such as floors and counters.

In one embodiment of this method, the surface is not rinsed with water after having been contacted with the composition. Rather, the surface is wiped or airdried.

The invention also pertains to a disinfecting composition suitable for cleaning inanimate hard surfaces comprising:
- 0.1-3 wt. %, in particular 0.1-2 wt. %, of one or more N-acylated amino acids or N-acylated peptides, or a salt thereof,
- less than 0.1 wt. % of hydrogen peroxide,
- 0.1-3 wt. %, in particular 0.1-2 wt. %, of one or more non-ethoxylated anionic surfactants,
- 0.05-2 wt. %, in particular 0.05-1 wt. %, of a carboxylic acid, wherein the disinfecting composition has a pH in the range of 1-3.5, in particular 1-3, wherein the composition comprises less than 2 wt. % of ethoxylated anionic surfactant, in particular less than 1 wt. %, more in particular less than 0.5 wt. %.

The composition described in the previous two paragraphs, and in general the compositions described in the present specification, can be obtained by diluting more concentrated solutions. The present invention thus also pertains to a method for disinfecting a surface which is contaminated with microorganisms or which is suspected of being contaminated with microorganisms, the microorganism being one or more of *Escherichia coli, Staphylococcus aureus, Pseudomonas aeruginosa*, and *Enterococcus hirae*, comprising the step of contacting the surface with a disinfecting composition comprising:
- 0.1-10 wt. % of one or more N-acylated amino acids or N-acylated peptides, or a salt thereof,
- less than 0.1 wt. % of hydrogen peroxide,
- 0.1-20 wt. % of one or more non-ethoxylated anionic surfactants,
- 0.05-5 wt. % of a carboxylic acid, wherein the disinfecting composition has a pH in the range of 1-4.5, wherein the composition comprises less than 5 wt. % of ethoxylated anionic surfactant, wherein the disinfecting composition is obtained by diluting a concentrated composition comprising one or more N-acylated amino acids or N-acylated peptides, one or more non-ethoxylated anionic surfactants, one or more carboxylic acids with water.

The degree of dilution generally is such that the concentrated composition can be diluted with water in a ratio of 1-25 wt. % (composition in water), in particular 2-20 wt. %, more specifically 5-20 wt. %.

It will be clear to the skilled person that the various embodiments and preferences describes herein can be combined, unless they are presented as mutually excluding alternatives.

The invention will be elucidated by the following examples, without being limited thereto or thereby.

EXAMPLES

To illustrate the compositions according to the invention and their effect as compared to the prior art, numerous compositions were prepared and tested. The compositions were prepared in distilled water using commercially available concentrated stocks of the various components.

Explanation of the Products Used

Ammonium Lauryl Sulfate (28% active, Texapon ALS, BASF)

Cocoglucoside (50% active, Plantacare 818, BASF)

Cocamide DEA (90% active, Comperlan COD, BASF)

Cocamidopropyl Betaine (30% active, Tego Betaine F, Degussa; Mackam CB 818, McIntyre; Genagen CAB 818, Clariant)

Cocamine Oxide (30% active, Genaminox CLS, Clariant)

Disodium Capryloyl Glutamate (40% active, Protelan AG 8, Zschimmer & Schwarz)

Disodium Cocoamphodiacetate (40% active, Dehyton DC, BASF)

Disodium Laureth Sulfosuccinate (40% active, Setacin 103 Zschimmer & Schwarz)

Glycol Stearate (Cutina EGMS, BASF)

Lauramidopropylbetaine (30% active, Mackam LAB, Rhodia)

Laureth-3 (Dehydol LS3, BASF)

MIPA Laureth Sulfate (59% active, Zetesol 2056, Zschimmer & Schwarz)

MIPA Lauryl Sulfate (60% active, Sulfetal CJOT 60, Zschimmer & Schwarz)

PEG-150 Distearate (Aculyn 60P, Dow)

PEG-40 Hydrogenated Castor Oil (90% active, Cremophor RH410, BASF)

PEG-9 Cocoglycerides (Oxypon 401, Zschimmer & Schwarz)

Polysorbate 20 (Tween 20, Croda)

Polysorbate 80 (Tween 80, Croda)

Potassium Undecylenoyl Hydrolyzed Wheat Protein (40% active, Protelan AG 11, Zschimmer & Schwarz)

Sodium C14-17 Sec Alkyl Sulfonate (30% active, Hostapur SAS 30, Clariant)

Sodium Cocoyl Glutamate (34% active, Protelan AGL 95 and Protelan AGL 95/C, Zschimmer & Schwarz)

Sodium Cocoyl Glycinate (30% active, Hostapur SG, Clariant)

Sodium Cocoyl Hydrolyzed Wheat Protein, (39% active, Protelan VE/K Zschimmer & Schwarz)

Sodium Cocoyl Isethionate (85% active, Hostapur SCI, Clariant)

Sodium Laureth Sulfate (70% active, Texapon N7, BASF; 28% active, Zetesol NL U, Zschimmer & Schwarz)

Sodium Lauroyl Sarcosinate (30% active, Protelan LS 9011, Zschimmer & Schwarz)

Sodium Lauryl Sulfate (97% active, Texapon K12G, BASF)

Triethanolamine Lauryl Sulfate (42% active, Texapon T42, BASF)

Zinc Coceth Sulfate (25% active, Zetesol Zn, Zschimmer & Schwarz)

Test Method

Biocidal activity of the various compositions was tested using a controlled bactericidal suspension test conform the European Norm for chemical disinfectants and antiseptics EN 1276 (EN 1276: Quantitative suspension test for the evaluation of bactericidal activity of chemical disinfectants and antiseptics used in food, industrial, domestic, and institutional areas: test method and requirements). The test protocol is as follows: One ml of a test suspension containing about $10^8$ cfu of the test microorganism per ml is added to 8 ml of the composition to be tested, and 1 ml milli-Q water is added. A soiled condition is simulated by adding 0.3% bovine albumin serum. After 1, 3 and 5 minutes contact time, the amount of viable bacteria was determined. The EN 1276 norm prescribes a log 5 reduction in viable cell count after a contact time of 5 minutes.

In the composition tables, all ingredients are indicated as wt. % and are calculated as active component. pm stands for amount added to achieve a certain effect. In particular, NaOH and phosphoric acid are often added 'pm' in amounts sufficient to obtain the specified pH.

In the results tables, the logarithmic reductions after a specific exposure time of the product to various microorganisms is indicated. Where the number is preceded by the indication ">" no colonies were found at all (which represents a complete kill of that specific organism), so the reduction was calculated from the amount of colony forming units in the start suspension and the subsequent dilution applied.

The indication "TNTC" stands for Too Numerous To Count. It is used where the number of colony forming units on the plate was too high to count, which means that no reduction in bacterial species could be detected, that is, no biocidal effect is found.

Example 1: Compositions According to the Invention

Various compositions according to the invention were prepared, and their biocidal activity was determined as indicated above. The following tables give the composition and biocidal effect of compositions 1.1 through 1.3 according to the invention.

| Ingredient Name (INCI) | 1.1 | 1.2 | 1.3 |
|---|---|---|---|
| water | to 100 | to 100 | to 100 |
| Triethanolamine Lauryl Sulfate | 4.20 | 4.20 | 10.50 |
| Disodium Capryloyl Glutamate | 2.00 | | |
| Potassium Undecylenoyl Hydolyzed wheat protein | | 1.80 | 3.60 |
| Sodium Lauroyl Sarcosinate | | | 1.50 |
| Cocoamidopropyl betaine | | | 1.50 |
| Lactic Acid | 1.29 | 1.26 | 3.59 |
| Glycerin | 1.00 | 1.00 | 1.00 |
| Allantoin | 0.20 | 0.20 | 0.20 |
| Aloe Barbadensis leaf extract | 1.00 | 1.00 | 1.00 |
| pH | 4.0 | 4.0 | 4.0 |

| | E. coli | | S. aureus | | E. hirae | |
|---|---|---|---|---|---|---|
| | 3 minutes | 5 minutes | 3 minutes | 5 minutes | 3 minutes | 5 minutes |
| 1.1 | TNTC | 4.8 | 5 | 6.3 | 5.2 | >5.2 |
| 1.2 | 4.9 | >5.7 | TNTC | 5.3 | >5.2 | >5.2 |
| 1.3 | TNTC | 4.7 | 5.2 | 6.6 | >5.2 | >5.2 |

The following tables give the composition and biocidal effect of compositions 2.1 through 2.6 according to the invention.

| Ingredient Name (INCI) | 2.1 | 2.2 | 2.3 | 2.4 | 2.5 | 2.6 |
|---|---|---|---|---|---|---|
| Water | to 100 | to 100 | to 100 | to 100 | to 100 | to 100 |
| Sodium Laureth Sulfate | | | | 2.80 | | |
| Triethanolamine Lauryl Sulfate | 4.20 | 4.20 | 4.20 | | | |
| Zink Laureth Sulfate | | | | | | 2.50 |
| Sodium Lauryl Sulfate | | | | 2.91 | 2.91 | 2.91 |
| Disodium Capryloyl Glutamate | 2.00 | | | 2.00 | | |
| Potassium Undecylenoyl Hydolyzed wheat protein | | 1.80 | 1.80 | | | 1.80 |
| Sodium Lauroyl Sarcosinate | | 1.50 | 1.50 | | | |
| Sodium Cocoyl Hydrolyzed Wheat Protein | | | | | 1.96 | |
| Lactic acid | 1.80 | 2.42 | 1.94 | 1.58 | 1.66 | 1.36 |
| Glycerin | 1.00 | 1.00 | 1.00 | 1.00 | 1.00 | 1.00 |
| Allantoin | 0.20 | 0.20 | 0.20 | 0.20 | 0.20 | 0.20 |
| Aloe Barbadensis leaf extract | 1.00 | 1.00 | 1.00 | 1.00 | 1.00 | 1.00 |
| Sodium Hydroxide | pm | pm | pm | pm | pm | pm |
| pH | 3.7 | 3.7 | 3.7 | 3.7 | 3.7 | 3.7 |

| | E. coli | | S. aureus | | E. hirae | |
|---|---|---|---|---|---|---|
| | 3 minutes | 5 minutes | 3 minutes | 5 minutes | 3 minutes | 5 minutes |
| 2.1 | TNTC | 4.8 | 6.7 | 5.8 | >5.2 | >5.2 |
| 2.2 | TNTC | 3.8 | 5.5 | >6.7 | >5.2 | >5.2 |
| 2.3 | 3.8 | 5.4 | 4.9 | 6.7 | >5.2 | >5.2 |
| 2.4 | >5.7 | >5.7 | >6.7 | >6.7 | >5.2 | >5.2 |
| 2.5 | >5.7 | >5.7 | 6.7 | >6.7 | >5.2 | >5.2 |
| 2.6 | 5.2 | >5.7 | 5 | 6.7 | >5.2 | >5.2 |

The following tables give the composition and biocidal effect of compositions 3.1 through 3.4 according to the invention:

| Ingredient Name (INCI) | 3.1 | 3.2 | 3.3 | 3.4 |
|---|---|---|---|---|
| Water | to 100 | to 100 | to 100 | to 100 |
| Sodium Laureth Sulfate | | 2.80 | | |
| Triethanolamine Lauryl Sulfate | 8.40 | | 8.40 | 5.04 |
| Sodium Lauryl Sulfate | | 2.91 | | |
| Disodium Capryloyl Glutamate | 2.00 | | | |
| Sodium Lauroyl Sarcosinate | | | | 1.80 |
| Sodium Cocoyl Glutamate | | 1.70 | | |
| Sodium Cocoyl Hydrolyzed Wheat Protein | | | | 1.68 |
| Cocoamidopropyl betaine | 1.50 | | 1.50 | |
| Lactic acid | 0.88 | 0.88 | 0.88 | 0.88 |
| Citric Acid | 0.80 | 0.50 | 0.50 | 0.50 |
| Glycerin | 1.00 | 1.00 | 1.00 | 1.00 |
| Allantoin | 0.20 | 0.20 | 0.20 | 0.20 |
| Aloe Barbadensis leaf extract | 1.00 | 1.00 | 1.00 | 1.00 |
| Sodium Hydroxide | pm | pm | pm | pm |
| pH | 3.7 | 3.7 | 3.7 | 3.7 |

| | E. coli | | S. aureus | | E. hirae | |
|---|---|---|---|---|---|---|
| | 3 minutes | 5 minutes | 3 minutes | 5 minutes | 3 minutes | 5 minutes |
| 3.1 | 3 | 4.1 | 4.6 | 4.6 | 4 | >5.0 |
| 3.2 | 4.1 | 4.1 | 4.6 | 4.6 | >5.0 | >5.0 |
| 3.3 | 4.1 | 4.1 | 4.6 | 4.6 | >5.0 | >5.0 |
| 3.4 | TNTC | 4.1 | 4.6 | 4.6 | >5.0 | >5.0 |

The following tables give the composition and biocidal effect of compositions 4.1 through 4.8 according to the invention.

| Ingredient Name (INCI) | 4.1 | 4.2 | 4.3 | 4.4 | 4.5 | 4.6 | 4.7 | 4.8 |
|---|---|---|---|---|---|---|---|---|
| Water | to 100 | to 100 | to 100 | to 100 | to 100 | to 100 | to 100 | to 100 |
| Triethanolamine Lauryl Sulfate | 2.10 | 2.10 | 4.20 | | | 0.84 | 1.68 | 2.52 |
| Sodium Lauryl Sulfate | | | | 1.94 | 1.94 | | | |
| Disodium Capryloyl Glutamate | | 0.80 | 2.00 | 0.80 | | 0.80 | 0.80 | 2.00 |
| Sodium Lauroyl Sarcosinate | 1.50 | 0.60 | | | 1.50 | | 0.60 | |
| Cocoamidopropyl betaine | | | 1.50 | | | | | |
| Lactic acid | 0.44 | | | | | 0.88 | 0.88 | |
| Citric Acid | 0.50 | | | | 0.50 | | | |
| Tartaric acid | | | 1.00 | 0.50 | | 0.50 | | 1.00 |
| Maleic acid | | | | 1.00 | 1.00 | | | |
| Benzoic acid | | | | | | 0.20 | 0.20 | 0.20 |
| Salicylic acid | | | | 0.10 | | | | |
| Phosphoric acid | 0.05 | 0.53 | 0.43 | 0.08 | 0.22 | | 0.06 | |
| Sodium Hydroxide | 0.06 | 0.36 | pm | 0.86 | pm | 0.3 | pm | pm |
| pH | 3.5 | 3.0 | 3.0 | 3.5 | 3.0 | 3.5 | 3.5 | 3.5 |

|     | E. coli |       | S. aureus |       |
| --- | ---     | ---   | ---       | ---   |
|     | 3 min   | 5 min | 3 min     | 5 min |
| 4.1 | 4       | 5.3   | >7.3      | >7.3  |
| 4.2 | >7.0    | >7.0  | >7.3      | >7.3  |
| 4.3 | 5.8     | 7     | >7.3      | >7.3  |
| 4.4 | 5.7     | 7     | >7.3      | >7.3  |
| 4.5 | >7.0    | >7.0  | >7.3      | >7.3  |
| 4.6 | 7       | >7.0  | >7.3      | >7.3  |
| 4.7 | 5.8     | >7    | >7.3      | >7.3  |
| 4.8 | 3.5     | 6.1   | >7.3      | >7.3  |

|     | E. hirae |       | P. aeruginosa |       |
| --- | ---      | ---   | ---           | ---   |
|     | 3 min    | 5 min | 3 min         | 5 min |
| 4.1 | >6.0     | >6.0  | 6             | >7.0  |
| 4.2 | >6.0     | >6.0  | >7.0          | >7.0  |
| 4.3 | >6.0     | >6.0  | 6.4           | >7.0  |
| 4.4 | 5.5      | >6.0  | >7.0          | >7.0  |
| 4.5 | >6.0     | >6.0  | >7.0          | >7.0  |
| 4.6 | >6.0     | >6.0  | >7.0          | >7.0  |
| 4.7 | >6.0     | >6.0  | >7.0          | >7.0  |
| 4.8 | >6.0     | >6.0  | >7.0          | >7.0  |

The following tables give the composition and biocidal effect of compositions 5.1 through 5.5 according to the invention.

| INCI | 5.1 | 5.2 | 5.3 | 5.4 | 5.5 |
| --- | --- | --- | --- | --- | --- |
| Water | to 100 | to 100 | to 100 | to 100 | to 100 |
| Triethanolamine Lauryl Sulfate |  |  |  | 4.20 | 4.20 |
| MIPA Lauryl Sulfate | 2.10 | 4.20 |  |  |  |
| Sodium C14-17 Sec Alkyl Sulfonate |  |  | 3.90 |  |  |
| Disodium Capryloyl Glutamate | 0.80 |  |  |  |  |
| Sodium Lauroyl Sarcosinate |  | 1.50 | 1.50 |  |  |
| Sodium Cocoyl Glycinate |  |  |  | 1.50 |  |
| Sodium Cocoyl Isethionate |  |  |  |  | 1.70 |
| Lactic acid | 0.88 |  | 0.53 | 0.88 |  |
| Citric acid |  | 1.00 |  |  | 0.80 |
| Maleic acid |  |  | 0.50 |  |  |
| Benzoic acid |  |  |  |  | 0.20 |
| Phosphoric acid | pm | 0.12 | 0.18 | 0.12 | pm |
| Sodium Hydroxide | 0.15 | pm | pm | pm | 0.1 |
| pH | 3.5 | 3.5 | 3.5 | 3.5 | 3.5 |

|     | E. coli |       | S. aureus |       |
| --- | ---     | ---   | ---       | ---   |
|     | 3 min   | 5 min | 3 min     | 5 min |
| 5.1 | 3       | 5.5   | 5.8       | >7.0  |
| 5.2 | 5.7     | >6.3  | >7.0      | >7.0  |
| 5.3 | 4       | 5.1   | >7.0      | >7.0  |
| 5.4 | 4.4     | 5.6   | 7.0       | >7.0  |
| 5.5 | 6.3     | >6.3  | 5.2       | >7.0  |

|     | E. hirae |       | P. aeruginosa |       |
| --- | ---      | ---   | ---           | ---   |
|     | 3 min    | 5 min | 3 min         | 5 min |
| 5.1 | >6.2     | >6.2  | 6.9           | 6.6   |
| 5.2 | >6.2     | >6.2  | >6.9          | >6.9  |
| 5.3 | >6.2     | >6.2  | >6.9          | >6.9  |
| 5.4 | >6.2     | >6.2  | >6.9          | >6.9  |
| 5.5 | >6.2     | >6.2  | >6.9          | >6.9  |

The following tables show the composition and biocidal effect of compositions 6.1 and 6.2 according to the invention.

| Ingredient Name (INCI) | 6.1 | 6.2 |
| --- | --- | --- |
| Water | to 100 | to 100 |
| Triethanolamine Lauryl Sulfate | 2.10 | 1.68 |
| Disodium Capryloyl Glutamate | 0.80 |  |
| Sodium Lauroyl Sarcosinate | 0.60 |  |
| Sodium Cocoyl Glutamate |  | 1.70 |
| Lactic acid |  | 0.88 |
| Tartaric acid | 1.00 |  |
| Salicylic acid |  | 0.10 |
| Phosphoric acid | pm | pm |
| Sodium Hydroxide | pm | pm |
| pH | 3.8 | 3.8 |

|     | E. coli |       | S. aureus |       |
| --- | ---     | ---   | ---       | ---   |
|     | 3 min   | 5 min | 3 min     | 5 min |
| 6.1 | >5.2    | >5.2  | >7.0      | >7.0  |
| 6.2 | 4.3     | >5.2  | 5.1       | 6.3   |

|     | E. hirae |       | P. aeruginosa |       |
| --- | ---      | ---   | ---           | ---   |
|     | 3 min    | 5 min | 3 min         | 5 min |
| 6.1 | >5.2     | >5.2  | >6.5          | >6.5  |
| 6.2 | >5.2     | >5.2  | >6.5          | >6.5  |

Example 2: Efficacy after Short Contact Times

To show the efficacy of the composition according to the invention after short contact times, the compositions 7.1 through 7.3 presented in the following table were prepared. The biocidal effect is presented in the further tables.

| Ingredient Name (INCI) | 7.1 | 7.2 | 7.3 |
| --- | --- | --- | --- |
| Water | to 100 | to 100 | to 100 |
| Triethanolamine Lauryl Sulfate | 4.20 |  |  |
| Sodium Lauryl Sulfate |  | 6.79 | 6.79 |
| Disodium Capryloyl Glutamate | 2.00 | 6.00 | 6.00 |
| Citric Acid |  | 10.00 | 7.00 |
| Tartaric acid | 1.00 |  |  |
| Benzoic acid | 0.50 |  |  |
| Octanoic acid |  | 2.00 | 2.00 |
| Isopropyl alcohol |  | 3.40 | 3.40 |
| Phosphoric acid | 0.60 | pm | pm |
| Sodium Hydroxide | pm | pm | pm |
| pH | 3.0 | 3.0 | 3.0 |

|     | E. coli | | | S. aureus | | |
| --- | --- | --- | --- | --- | --- | --- |
|     | 1 min | 3 min | 5 min | 1 min | 3 min | 5 min |
| 7.1 | >7.0 | >7.0 | >7.0 | >7.3 | >7.3 | >7.3 |
| 7.2 | 6.7 | 6.3 | >7.2 | >7.2 | >7.2 | 6.7 |
| 7.3 | >7.2 | 7.2 | 7.2 | >7.2 | >7.2 | 7.1 |

|     | E. hirae | | | P. aeruginosa | | |
| --- | --- | --- | --- | --- | --- | --- |
|     | 1 min | 3 min | 5 min | 1 min | 3 min | 5 min |
| 7.1 | >6.0 | >6.0 | >6.0 | >7.0 | >7.0 | >7.0 |
| 7.2 | 5.5 | >5.5 | >5.5 | >7.0 | >7.0 | >7.0 |
| 7.3 | 5.5 | >5.5 | 5.2 | >7.0 | 7.0 | 7.0 |

As can be seen from the above tables these compositions according to the invention show high efficacy already after very short contact times, which evidences the fast disinfection effect of the compositions according to the invention against all four organisms.

Example 3: Effect of the Nature of the Surfactant

To investigate the effect of the nature of the surfactant, compositions where prepared which have essentially the same composition but wherein an ethoxylated anionic surfactant is used instead of a non-ethoxylated anionic surfactant. The compositions properties and results are presented in the following table.

|     | a inv | 1 comp | 2 comp |
| --- | --- | --- | --- |
| Water | to 100 | to 100 | to 100 |
| Triethanolamine Lauryl Sulfate | 4.20 |     |     |
| Ammonium Laureth Sulfate |     | 2.80 |     |
| Zinc Laureth Sulfate |     |     | 2.50 |
| Disodium Caproyl Glutamate | 2.00 | 2.00 | 2.00 |
| Lactic Acid | 1.29 | 1.08 | 0.85 |
| Glycerin | 1.00 | 1.00 | 1.00 |
| Allantoin | 0.20 |     | 0.20 |
| Aloe barbadensis leaf extract | 1.00 | 1.00 | 1.00 |
| pH | 4.0 | 4.0 | 4.0 |
| E. coli after 3 minutes | TNTC | TNTC | TNTC |
| E. coli after 5 minutes | 4.8 | TNTC | TNTC |
| S. aureus after 3 minutes | 5.0 | TNTC | TNTC |
| S. aureus after 5 minutes | 6.3 | TNTC | TNTC |
| E. hirae after 3 minutes | 5.2 | TNTC | TNTC |
| E. hirae after 5 minutes | >5.2 | TNTC | TNTC |

As can be seen from the table, the composition according to the invention is effective against all three organisms after 5 minutes, and against S. aureus and E. hirae also after three minutes. In contrast, comparable compositions which contain an ethoxylated anionic surfactant instead of a non-ethoxylated surfactant do not show any activity under these conditions. This is in particular remarkable for zinc laureth sulphate for which it is often believed that it shows biocidal activity.

Example 4: Effect of the Presence of N-Acylated Amino Acids or N-Acylated Peptide To investigate the effect of the presence of an N-acylated amino acid or N-acylated peptide, compositions where prepared which have essentially the same composition but wherein an N-acylated amino acid or N-acylated peptide is present, or re-placed by a polysorbate compound.

The compositions properties and results are presented in the following tables.

|     | ai inv | 3 comp | 4 comp |
| --- | --- | --- | --- |
| Water | to 100 | to 100 | to 100 |
| Triethanolamine lauryl Sulfate | 2.10 | 2.10 | 2.10 |
| Disodium Caproyl Glutamate | 0.80 |     |     |
| Sodium Lauroyl Sarcosinate | 0.60 |     |     |
| Tartaric Acid | 1.00 | 1.00 | 1.00 |
| Polysorbate-20 |     | 2.00 |     |
| Polysorbate-80 |     |     | 2.00 |
| Phosphoric acid (pH adjustment) | pm | pm | pm |
| Sodium Hydroxide (pH adjustment) | pm | pm | pm |
| pH | 3.8 | 3.8 | 3.8 |
| E. coli after 3 minutes | >5.2 | TNTC | TNTC |
| E. coli after 5 minutes | >5.2 | TNTC | TNTC |
| S. aureus after 3 minutes | >7.0 | TNTC | TNTC |
| S. aureus after 5 minutes | >7.0 | TNTC | TNTC |
| E. hirae after 3 minutes | >5.2 | 3.1 | 3.2 |
| E. hirae after 5 minutes | >5.2 | >5.2 | 4.5 |
| P aeruginosa after 3 minutes | >6.5 | 4.2 | 5.8 |
| P aeruginosa after 5 minutes | >6.5 | 6 | >6.5 |

|     | aj inv | 5 comp | 6 comp |
| --- | --- | --- | --- |
| Water | to 100 | to 100 | to 100 |
| Triethanolamine Lauryl Sulfate | 1.68 | 1.68 | 1.68 |
| Sodium Cocoyl Glutamate | 1.70 |     |     |
| Lactic Acid | 0.88 | 0.88 | 0.88 |
| Salicylic Acid | 0.10 | 0.10 | 0.10 |
| Polysorbate-20 |     | 2.00 |     |
| Polysorbate-80 |     |     | 2.00 |
| Phosphoric Acid (pH adjustment) | pm | pm | pm |
| Sodium Hydroxide (pH adjustment) | pm | pm | pm |
| pH | 3.8 | 3.8 | 3.8 |
| E. coli after 3 minutes | 4.3 | TNTC | TNTC |
| E. coli after 5 minutes | >5.2 | TNTC | TNTC |
| S. aureus after 3 minutes | 5.1 | TNTC | TNTC |
| S. aureus after 5 minutes | 6.3 | TNTC | TNTC |
| E. hirae after 3 minutes | >5.2 | TNTC | TNTC |
| E. hirae after 5 minutes | >5.2 | 4 | TNTC |
| P aeruginosa after 3 minutes | >6.5 | 5.3 | TNTC |
| P aeruginosa after 5 minutes | >6.5 | 6.5 | TNTC |

As can be seen from the tables above, compositions ai and aj according to the invention show activity against all microorganisms. In contrast, compositions containing a polysorbate instead of an N-acylated amino-acid do not show any activity against E. coli and S. aureus.

Example 5: Investigation of the Biocidal Effect of Prior Art Compositions—not in Accordance with the Present Invention The tables below show compositions as described in the prior art, and the results of teste performed using these compositions.

Examples 4, 5 and 6 (Beispiel 4, 5 and 6) from DE19838034A

Examples 1 and 2 from the Zschimmer & Schwarz brochure on Protelan AG8

Baby Shampoo, two Foam Baths, a Shower Gel, and 2 Shampoos from the Zschimmer & Schwarz brochure on Protelan VE/K Example 6 ("Cleaning Composition") from EP1074247A2.

As can be seen from the test results, no reduction in bacterial growth was detected at any contact time for any organism. Thus, none of the compositions show any measurable bactericidal effect.

| Ingredient Name (INCI) | DE19838034A1 Beispiel 4 | Beispiel 5 | Beispiel 6 | Z&S—Protelan AG 8 brochure Z&S 1 | Z&S 2 |
|---|---|---|---|---|---|
| Aqua | To 100 | To 100 | To 100 | To 100 | To 100 |
| Sodium Laureth Sulfate | 11.83 | 9.63 | 6.88 | 5.50 | 11.00 |
| Zink Coceth Sulfate | | | | 6.00 | |
| Disodium Capryloyl Glutamate | | | | 1.60 | 1.88 |
| Potassium Undecylenoyl Hydolyzed wheat protein | | | | 1.08 | |
| Sodium Lauroyl Sarcosinate | | | | 0.60 | 0.81 |
| Sodium Cocoyl Glutamate | 1.13 | 0.75 | 0.50 | | 0.68 |
| Cocamide DEA | | | | | 1.80 |
| Cocoamidopropyl Betaine | 3.63 | 2.64 | 4.62 | 2.10 | |
| Disodium Laureth Sulfosuccinate | | | | | 1.88 |
| Cocoglucoside | 1.00 | 2.00 | 1.50 | | |
| PEG-40 Hydrogenated Castor Oil | 0.5 | 0.5 | 0.5 | | |
| PEG-200 Glyceryl Palmitate | 0.5 | 0.5 | 0.5 | | |
| Sodium Benzoate | 0.45 | 0.45 | 0.45 | | |
| Sodium Salicylate | 0.2 | 0.2 | 0.2 | | |
| Citric Acid | 0.5 | 0.5 | 0.5 | 0.5 | |
| Lactic Acid | | | | | 0.89 |
| Panthenol | | | | 0.75 | |
| Sodium Chloride | | | | 2.5 | |
| Sodium Hydroxide | 0.27 | 0.37 | 0.68 | 0.62 | |
| pH | 5.6 | 5.5 | 5.4 | 5.5 | 5.0 |

| Ingredient Name (INCI) | Z&S - Protelan VE/K Brochure | | | | | | EP1074247 example 6 |
|---|---|---|---|---|---|---|---|
| | Baby Shampoo | Foam Bath | Foam Bath | Shower Gel | Shampoo | Shampoo | Cleansing composition |
| Aqua | To 100 | To 100 | To 100 | To 100 | To 100 | To 100 | To 100 |
| Sodium Laureth Sulfate | 8.40 | 17.50 | | 19.60 | 11.20 | | |
| Ammonium Lauryl Sulfate | | | | | | 10.08 | |
| Zink Laureth Sulfate | | | | | | | 7.50 |
| MIPA Laureth Sulfate | | 0.75 | 12.98 | 0.75 | | | |
| Sodium Lauryl Sulfate | | | | | | | 1.96 |
| Sodium Cocoyl Hydrolyzed Wheat Protein | 7.80 | 1.37 | 0.78 | 1.17 | 1.17 | 0.78 | 1.56 |
| Laureth-3 | | | | | | 0.5 | |
| PEG-150 Distearate | 0.5 | | | | | | |
| Polysorbate 20 | 3 | | | | | | |
| Cocamine Oxide | | | | | 0.90 | | |
| Lauramidopropylbetaine | | | | | | | 1.20 |
| Cocoamidopropyl Betaine | | | 2.70 | | 0.90 | | |
| Disodium Cocoamphodiacetate | | 2.00 | | 1.60 | | 2.80 | |
| Disodium Laureth Sulfosuccinate | | | | 1.60 | | 1.60 | |
| Sodium Benzoate | 0.15 | 0.15 | 0.15 | 0.15 | 0.15 | 0.15 | |
| Citric Acid | | 0.24 | | | | 0.26 | |
| Lactic Acid | 1.06 | | | pm | 0.46 | | pm |
| Glycol Stearate | | 0.20 | | 0.20 | | | |
| Panthenol | | | 1 | | | | |
| Sodium Chloride | | 1 | | 1 | 2.4 | | |
| Aloe Barbadensis leaf extract | | | | 0.55 | | | |
| Bisabolol | | | 0.1 | | | | |
| PEG-9 Cocoglycerides | | | 2.00 | | | | |
| Sodium Hydroxide | | 0.21 | 0.07 | 0.1 | | 0.48 | |
| pH | 5.5 | 6.0 | 6.3 | 5.5 | 6.0 | 6.0 | 6.0 |

| | | E. coli | | S. aureus | | E. hirae | |
|---|---|---|---|---|---|---|---|
| | RESULTS: | 3 minutes | 5 minutes | 3 minutes | 5 minutes | 3 minutes | 5 minutes |
| DE19838034A1 | Beispiel 4 | TNTC | TNTC | TNTC | TNTC | TNTC | TNTC |
| DE19838034A1 | Beispiel 5 | TNTC | TNTC | TNTC | TNTC | TNTC | TNTC |
| DE19838034A1 | Beispiel 6 | TNTC | TNTC | TNTC | TNTC | TNTC | TNTC |
| Z&S - Protelan AG 8 brochure | Z&S 1 | TNTC | TNTC | TNTC | TNTC | TNTC | TNTC |
| Z&S - Protelan AG 8 brochure | Z&S 2 | TNTC | TNTC | TNTC | TNTC | TNTC | TNTC |
| Z&S - Protelan VE/K Brochure | Baby Shampoo | TNTC | TNTC | TNTC | TNTC | TNTC | TNTC |
| Z&S - Protelan VE/K Brochure | Foam Bath | TNTC | TNTC | TNTC | TNTC | TNTC | TNTC |

-continued

|  |  | E. coli | | S. aureus | | E. hirae | |
|---|---|---|---|---|---|---|---|
| RESULTS: | | 3 minutes | 5 minutes | 3 minutes | 5 minutes | 3 minutes | 5 minutes |
| Z&S - Protelan VE/K Brochure | Foam Bath | TNTC | TNTC | TNTC | TNTC | TNTC | TNTC |
| Z&S - Protelan VE/K Brochure | Shower Gel | TNTC | TNTC | TNTC | TNTC | TNTC | TNTC |
| Z&S - Protelan VE/K Brochure | Shampoo | TNTC | TNTC | TNTC | TNTC | TNTC | TNTC |
| Z&S - Protelan VE/K Brochure | Shampoo | TNTC | TNTC | TNTC | TNTC | TNTC | TNTC |
| EP1074247A2 example 6 | Cleansing Comp. | TNTC | TNTC | TNTC | TNTC | TNTC | TNTC |

As can be seen from the table above, none of the prior art compositions shows any biocidal effect.

Example 6: Effect of pH

To investigate the effect of pH, various compositions were prepared which only differ in their pH. The pH was adjusted using sodium hydroxide. Experiments were carried out for lactic acid and tartaric acid. The results are presented in the following tables.

| Lactic acid | | | | |
|---|---|---|---|---|
|  | 8.1 | 8.2 | 8.3 | 8.4 |
| Deionised water | Ad 100 | Ad 100 | Ad 100 | Ad 100 |
| Triethanolamine Lauryl Sulfate | 4.20 | 4.20 | 4.20 | 4.20 |
| Sodium Capryloyl Glutamate | 2.00 | 2.00 | 2.00 | 2.00 |
| Sodium Lauryl Sulfate | 0.49 | 0.49 | 0.49 | 0.49 |
| Lactic Acid | 2.79 | 2.79 | 2.79 | 2.79 |
| Glycerin | 1.00 | 1.00 | 1.00 | 1.00 |
| Aloe vera | 1.00 | 1.00 | 1.00 | 1.00 |
| Allantoin | 0.20 | 0.20 | 0.20 | 0.20 |
| pH | 3.5 | 4.0 | 4.5 | 5.0 |
| E. coli | | | | |
| 30 sec | TNTC | TNTC | TNTC | TNTC |
| 1 minute | TNTC | TNTC | TNTC | TNTC |
| 3 minutes | 7.1 | TNTC | TNTC | TNTC |
| 5 minutes | >7.1* | 5.6 | TNTC | TNTC |
| S. aureus | | | | |
| 30 sec | 4 | <4.0 | TNTC | TNTC |
| 1 minute | 7 | 5.3 | TNTC | TNTC |
| 3 minutes | 7 | >7.0 | 4 | 4 |
| 5 minutes | 7 | >7.0 | 6.6 | 5.7 |
| E. hirae | | | | |
| 30 sec | <2.7 | 2.7 | <2.7 | TNTC |
| 1 minute | 5.7 | 4.5 | 2.7 | 2.7 |
| 3 minutes | >5.7 | 5.4 | 5.7 | >5.7 |
| 5 minutes | 4.9 | >5.7 | >5.7 | 5.4 |

| Tartaric acid | | | | |
|---|---|---|---|---|
|  | 8.5 | 8.6 | 8.7 | 8.8 |
| Deionised water | Ad 100 | Ad 100 | Ad 100 | Ad 100 |
| Triethanolamine Lauryl Sulfate | 4.20 | 4.20 | 4.20 | 4.20 |
| Sodium Capryloyl Glutamate | 2.00 | 2.00 | 2.00 | 2.00 |
| Sodium Lauryl Sulfate | 0.49 | 0.49 | 0.49 | 0.49 |
| Tartaric Acid | 1.54 | 1.54 | 1.54 | 1.54 |
| Glycerin | 1.00 | 1.00 | 1.00 | 1.00 |
| Aloe vera | 1.00 | 1.00 | 1.00 | 1.00 |
| Allantoin | 0.20 | 0.20 | 0.20 | 0.20 |
| pH | 3.5 | 4.0 | 4.5 | 5.0 |
| E. coli | | | | |
| 30 sec | TNTC | TNTC | TNTC | TNTC |
| 1 minute | TNTC | TNTC | TNTC | TNTC |
| 3 minutes | TNTC | TNTC | TNTC | TNTC |
| 5 minutes | 5.7 | TNTC | TNTC | TNTC |
| S. aureus | | | | |
| 30 sec | 5.2 | 4 | TNTC | TNTC |
| 1 minute | >7.0 | 5.9 | <4.0 | TNTC |
| 3 minutes | >7.0 | 7 | >7.0 | 6 |
| 5 minutes | 6.6 | >7.0 | 7 | 6.6 |
| E. hirae | | | | |
| 30 sec | 3.9 | 2.7 | <2.7 | <2.7 |
| 1 minute | >5.7 | 4.7 | 4.7 | 5.1 |
| 3 minutes | >5.7 | >5.7 | >5.7 | >5.7 |
| 5 minutes | >5.7 | >5.7 | >5.7 | >5.7 |

From the tables it can be concluded that pH plays an important role in the effectiveness of the composition. A pH of 3.5 works better than 4.0 or 4.5. A pH level of 4.5 is the maximum to achieve a certain efficacy for several organisms.

The invention claimed is:

1. Method for disinfecting a surface which is contaminated with microorganisms or which is suspected of being contaminated with microorganisms, the microorganism being one or more of *Escherichia coli, Staphylococcus aureus, Pseudomonas aeruginosa*, and *Enterococcus* hirae, comprising the step of contacting the surface with a disinfecting composition comprising:
   0.1-10 wt. % of one or more N-acylated amino acids or N-acylated peptides, or a salt thereof,
   less than 0.1 wt. % of hydrogen peroxide,
   0.1-20 wt. % of one or more non-ethoxylated anionic surfactants, wherein the one or more non-ethoxylated anionic surfactants are selected from the group consisting of an alkyl sulfate salt, wherein the alkyl chain comprises 4-22 carbon atoms, a sulphonate salt selected from the group consisting of an alkyl sulphonate salt, an alkyl sulfoacetate salt, an alkyl sulfosuccinate salt and a sulfolaurate salt, and combinations thereof,
   0.05-5 wt. % of one or more carboxylic acids, wherein each carboxylic acid has 2 to 10 carbon atoms,
   wherein the disinfecting composition has a pH in the range of 1-4, wherein the composition comprises less than 5 wt. % of ethoxylated anionic surfactant.

2. Method according to claim 1, wherein the surface is a surface of the animal or human body, and the composition has a pH in the range of 3-4.

3. Method according to claim 1, wherein the surface is an inanimate surface.

4. Method according to claim 1, wherein the disinfecting composition comprises 0.2-8 wt. % of one or more N-acylated amino acids or N-acylated peptides, or a salt thereof, wherein the N-acylated amino acids or N-acylated peptides has a structure according to Formula I as follows:

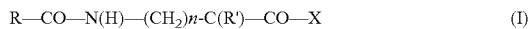
R—CO—N(H)—(CH₂)n-C(R')—CO—X    (I)

or a salt thereof,
wherein R—CO— represents an acyl group wherein R is a saturated or unsaturated, straight of branched C5 to C21 radical,
n is 0, 1 or 2,
R' represents an amino acid side chain, and
X is OH or a group according to Formula II:

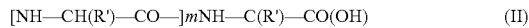
[NH—CH(R')—CO—]mNH—C(R')—CO(OH)    (II)

wherein m ranges from 0 to such a value that the compound of Formula II specifies a peptide having an average molecular weight of about 100 to about 3900 Dalton.

5. Method according to claim 1, wherein disinfecting composition comprises 0.2-15 wt. % of one or more non-ethoxylated anionic surfactants.

6. Method according to claim 1, wherein the composition comprises less than 3 wt. % of ethoxylated anionic surfactant.

7. Method according to claim 1, wherein the composition comprises 0.1-3 wt. % of the one or more carboxylic acids.

8. Method according to claim 1, wherein the one or more carboxylic acids are a cyclic carboxylic acid selected from the group of 2-furan-dicarboxylic acid, (iso)phthalic acid, furoic acid, salicylic acid and/or benzoic acid.

9. Method according to claim 1, wherein the surface is contaminated or suspected to be contaminated with *Escherichia coli, Staphylococcus aureus, Pseudomonas aeruginosa,* and *Enterococcus hirae.*

10. Method according to claim 1, wherein the surface to be disinfected is selected from skin, hair, or mucous membranes in healthcare environments or inanimate surfaces in healthcare environments.

11. Method according to claim 1 where the surface may be rinsed with water or wiped to dry, or not rinsed or wiped and left to air dry.

12. Method according to claim 1, wherein the composition comprises at least one of the following carboxylic acids: lactic acid, glycolic, acid, benzoic acid, and tartaric acid.

13. Method according to claim 1, wherein an inanimate hard surface is contacted with a disinfecting composition comprising:
0.1-3 wt. % of one or more N-acylated amino acids or N-acylated peptides, or a salt thereof,
less than 0.1 wt. % of hydrogen peroxide,
0.1-3 wt. % of one or more of the non-ethoxylated anionic surfactants,
0.05-2 wt. % of the one or more carboxylic acids,
wherein the disinfecting composition has a pH in the range of 1-3.5, wherein the composition comprises less than 2 wt. % of ethoxylated anionic surfactant.

14. Method according to claim 13, wherein the surface is not rinsed with water after having been contacted with the composition.

15. Method according to claim 1, wherein the disinfecting composition is obtained by diluting a more concentrated composition with water, wherein the concentrated solution is generally diluted with water in a ratio of 1 to 25 wt. % (product in water).

16. Disinfecting composition suitable for disinfecting a surface which is contaminated with microorganisms or which is suspected of being contaminated with microorganisms, the microorganism being one or more of *Escherichia coli, Staphylococcus aureus, Pseudomonas aeruginosa,* and *Enterococcus hirae,* the composition comprising
0.1-10 wt. % of one or more N-acylated amino acids or N-acylated peptides, or a salt thereof,
less than 0.1 wt. % of hydrogen peroxide,
0.1-20 wt. % of one or more non-ethoxylated anionic surfactants, wherein the one or more non-ethoxylated anionic surfactants are selected from the group consisting of an alkyl sulfate salt, wherein the alkyl chain comprises 4-22 carbon atoms, a sulphonate salt selected from the group consisting of an alkyl sulphonate salt, an alkyl sulfoacetate salt, an alkyl sulfosuccinate salt and a sulfolaurate salt, and combinations thereof,
0.05-5 wt. % of one or more carboxylic acids, wherein each carboxylic acid has 2 to 10 carbon atoms,
wherein the disinfecting composition has a pH in the range of 1-4, wherein the composition comprises less than 5 wt. % of ethoxylated anionic surfactant.

17. Disinfecting composition according to claim 16, which comprises:
0.1-3 wt. % of one or more N-acylated amino acids or N-acylated peptides, or a salt thereof,
less than 0.1 wt. % of hydrogen peroxide,
0.1-3 wt. % of one or more of the non-ethoxylated anionic surfactants,
0.05-2 wt. % of the one or more carboxylic acids,
wherein the disinfecting composition has a pH in the range of 1-3.5 wherein the composition comprises less than 2 wt. % of ethoxylated anionic surfactant.

18. Method according to claim 1, wherein the composition comprises at least one of the following carboxylic acids: citric acid, lactic acid, glycolic acid, tartaric acid, malic acid, maleic acid, fumaric acid, adipic acid, and succinic acid.

* * * * *